United States Patent [19]

Cevasco et al.

[11] Patent Number: 5,225,560
[45] Date of Patent: Jul. 6, 1993

[54] PROCESS FOR THE PREPARATION OF DIALKYL PYRIDINE-2,3-DICARBOXYLATE AND DERIVATIVES THEREOF FROM DIALKYL DICHLOROSUCCINATE

[75] Inventors: Albert A. Cevasco, Belle Mead; George A. Chiarello, Yardville; William F. Rieker, Clarke, all of N.J.

[73] Assignee: American Cyanamid Company, Stamford, Conn.

[21] Appl. No.: 803,855

[22] Filed: Dec. 9, 1991

Related U.S. Application Data

[63] Continuation-in-part of Ser. No. 538,862, Jun. 15, 1990, Pat. No. 5,124,458.

[51] Int. Cl.$^5$ .................. C07D 213/08; C07D 213/80; C07D 213/803
[52] U.S. Cl. ..................................... 546/250; 546/299; 546/321; 546/251

[58] Field of Search ................ 546/250, 251, 299, 321

[56] References Cited

U.S. PATENT DOCUMENTS

| | | | |
|---|---|---|---|
| 4,723,011 | 2/1988 | Doehner, Jr. | 546/250 |
| 4,758,667 | 7/1988 | Szczepanski et al. | 546/167 |
| 4,798,619 | 1/1989 | Los | 71/66 |
| 4,871,859 | 10/1989 | Gupton et al. | 546/250 |
| 4,948,896 | 8/1990 | Nagao | 546/250 |
| 5,008,392 | 4/1991 | Meier et al. | 546/250 |

Primary Examiner—Alan L. Rotman
Attorney, Agent, or Firm—Peggy A. Climenson

[57] ABSTRACT

There is provided a process for the preparation of substituted and unsubstituted-2,3-pyridinedicarboxylate compounds by reacting a dialkyl dichlorosuccinate with a dehydrohalogenating agent, an ammonia source and an appropriately substituted $\alpha,\beta$-unsaturated aldehyde or ketone.

16 Claims, No Drawings

PROCESS FOR THE PREPARATION OF DIALKYL PYRIDINE-2,3-DICARBOXYLATE AND DERIVATIVES THEREOF FROM DIALKYL DICHLOROSUCCINATE

This is a continuation-in-part of copending U.S. application Ser. No. 07/538,862, filed on Jun. 15, 1990, now U.S. Pat. No. 5,124,458, issued on Jun. 23, 1992.

BACKGROUND OF THE INVENTION

Pyridine-2,3-dicarboxylates are useful intermediates in the preparation of highly effective herbicidal 2-(2-imidazolin-2-yl)nicotinic acids, esters and salts. Said herbicidal agents and methods for their preparation are disclosed in U.S. Pat. No. 4,798,619 and U.S. Pat. No. 4,758,667. Imidazolinyl nicotinates and derivatives thereof are highly effective herbicides at low rates of application which demonstrate selective control of noxious weeds in the presence of important agronomic crops while exhibiting exceptionally low mammalian toxicity.

Processes for the preparation of substituted pyridine-2,3-dicarboxylates are described in U.S. Pat. Nos. 4,723,011; 4,871,859; 4,948,896 and 5,008,392 among others. However, there is a need in the art for yet more suitable methods of preparation for these important intermediates.

It is an object of this invention to provide an efficient and effective method for the preparation of substituted and unsubstituted-2,3-pyridinedicarboxylates utilizing dialkyl dichlorosuccinate, a dehydrohalogenating agent, an ammonia source and an appropriately substituted-α,β-unsaturated aldehyde or ketone.

SUMMARY OF THE INVENTION

The invention herein described relates to a novel method for the preparation of substituted and unsubstituted 2,3-pyridinedicarboxylates of formula I

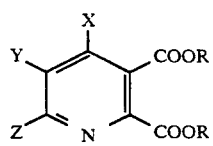

wherein R is $C_1$–$C_6$ alkyl; X is hydrogen, halogen, $C_1$–$C_4$ alkyl, $C_1$–$C_4$ alkoxy or $C_2$–$C_5$ alkenyl; Z is hydrogen, $C_1$–$C_4$ alkyl or $C_2$–$C_5$ alkenyl and Y is hydrogen, halogen, $C_1$–$C_6$ alkyl optionally substituted with one to three halogens, hydroxy groups, $C_1$–$C_4$ alkoxy groups or $C_1$–$C_4$ alkylthio groups, $C_1$–$C_4$ alkoxycarbonyl, aminocarbonyl, phenyl, substituted phenyl, phenoxy, substituted phenoxy, phenylthio or substituted phenylthio. Compounds of formula I are useful as intermediates in the preparation of herbicidal 2-(2-imidazolin-2-yl)nicotinates. Among the methods of preparation of said herbicidal nicotinates is that described in U.S. Pat. No. 4,758,667 and illustrated below.

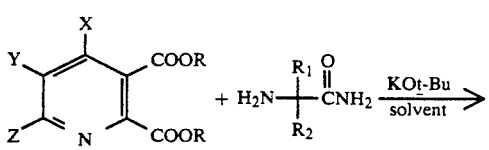

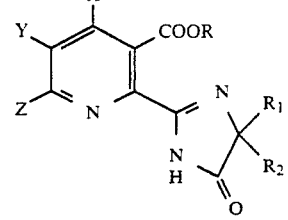

wherein $R_1$ is hydrogen or $C_1$–$C_4$ alkyl; $R_2$ hydrogen, halogen, $C_1$–$C_4$ alkyl, $C_3$–$C_6$ cycloalkyl or $R_1$ and $R_2$ may be taken together to form a $C_3$–$C_6$ cycloalkyl optionally substituted with methyl and X, Y and Z are as described for formula U.

DETAILED DESCRIPTION OF THE INVENTION

It has now been found that pyridine-2,3-dicarboxylates of formula I can be efficiently and effectively prepared from dialkyl dichlorosuccinates of formula II by reacting said succinate with at least one molar equipment of a dehydrohalogenating agent such as ammonium acetate or trialkylamine in the presence of a solvent such as a lower alkylalcohol to form an intermediate, reacting said intermediate with a source of ammonia, optionally at elevated temperatures to form a second intermediate and reacting said second intermediate with at least one molar equivalent of an α,β-unsaturated aldehyde or ketone of formula III wherein X, Y and Z are as described above for formula I in the presence of an acid such as formic acid or acetic acid or the like. The process is shown below.

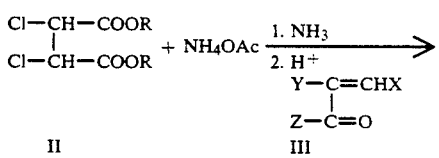

Dehydrohalogenating agent suitable for use in the process of the invention are those which may also serve as an ammonia source such as ammonium acetate, ammonium carbonates, ammonium carbamates, ammonium sulfamates and the like. Also suitable are reagents such as trialkylamines, pyridines, picolines, quaternary amine salts such as tetraalkylammonium halides and the like. Of course, in addition to the above-mentioned ammonia sources, ammonia itself may be employed in the process of the invention.

In one embodiment of the invention the solvent utilized may be a polar solvent such as an alcohol, a nitrile such as acetonitrile, a carboxylic acid amide such as N,N-dimethylformamide, N-methylpyrrolidone, a sulfoxide such as dimethylsulfoxide, a sulfone and the like.

Among the α,β-unsaturated aldehydes or ketones of formula III which can be used in the process of the invention are acrolein, methacrolein, ethacrolein, crotonaldehyde, methyl vinyl ketone, α-n-butylacrolein, 4-methyl-2-hexanal, α-methoxymethacrolein, α-chloromethacrolein, α-trifluoromethacrolein, cinnamaldehyde, α-ethoxyacrolein, methyl α-formylacrylate, α-(2-cyanoethyl) acrolein and the like.

In a further embodiment of the invention, the reaction mixture comprising the above-formed second intermediate and the α,β-unsaturated aldehyde or ketone of formula III may be treated with a dehydrogenation catalyst such as that which is conventional in the art including metals or compounds of platinum, palladium, ruthenium, iridium, nickel, iron, copper, antimony, cobalt, rhodium and the like. The dehydrogenation catalyst is commonly used in the form of the dehydrogenation metal or compound thereof deposited on a suitable support such as alumina, carbon, clay, zeolite, chromia, zirconia and the like.

Utilizing the process of the invention, pyridine-2,3-dicarboxylates containing substituents in the 4,5 and 6 positions may be conveniently prepared by admixing a formula II dialkyl dichlorosuccinate with at least one molar equivalent of a dehydrohalogenating agent in a suitable solvent, optionally filtering off insolubles, treating the filtrate or unfiltered reaction mixture with anhydrous ammonia, optionally heating said reaction mixture until the formation of the enamine intermediate is complete, optionally filtering off insolubles, adding to the filtrate or to the unfiltered reaction mixture an acid such as a mineral acid, sulfuric acid, phosphoric acid, an organic acid such as formic acid, acetic acid or propionic acid and the like, and treating with at least one molar equivalent of an α,β-unsaturated aldehyde or ketone of formula III optionally adding a dehydrogenation catalyst, optionally heating the resulting reaction mixture until the formation of the formula I pyridinedicarboxylate is complete.

After completion of the reaction, the desired pyridine-2,3-dicarboxylate can be isolated and purified using conventional methods such as extraction, distillation, recrystallization, chromatography and the like.

The rate of formation of the enamine second intermediate and the formula I product is temperature dependent, thus, reaction time can be effectively reduced by heating the reaction mixtures at temperatures of about 45° C. or greater.

In order to facilitate a further understanding of the invention, the following examples are presented primarily for the purpose of illustrating certain more specific details thereof and the invention is not to be deemed limited thereby. The terms $^1$HNMR and IR designate proton nuclear magnetic resonance and infrared, respectively. Unless otherwise noted, all parts are parts by weight.

EXAMPLE 1

Preparation of diethyl 5-ethyl-2,3-pyridinedicarboxylate from diethyl dichlorosuccinate using ammonium acetate A stirred mixture of diethyl dichlorosuccinate (12.2 g, 0.05 mole) and ammonium acetate (15.4 g, 0.20 mole) in absolute ethanol is heated at 60° C. for 6 hours, cooled to 20° C., treated with excess anhydrous ammonia (5.0 g, 0.29 mole), heated at 60° C. for 4½ hours, partially distilled to remove excess ammonia, cooled to 30° C. and filtered. The filter cake is washed with ethanol and the filtrates are combined and concentrated in vacuo. The thus-concentrated reaction solution is treated with acetic acid, treated dropwise with an ethanolic solution of 2-ethacrolein at 70° C. over a 1½ hour period, continued heating at 70° C. for 4 hours (until reaction is complete by gas chromatographic analysis) and concentrated in vacuo to give a crude oil residue. The oil residue is distilled to afford the title product as a tan oil, bp 151°–152° C. 2mm Hg.

EXAMPLE 2

Preparation of diethyl 5-ethyl-2,3-pyridinedicarboxylate from diethyl dichlorosuccinate using triethylamine A solution of diethyl dichlorosuccinate (24.6 g, 0.10 mole) in ethanol is treated with triethylamine (12.2 g, 0.12 mole) over a 5 minute period, allowed to stir at ambient temperatures for 12 hours, treated with anhydrous ammonia (7.3 g, 0.43 mol) at 20° C., heated at 45°–50° C. for 3 hours and filtered. The filter cake is washed with ethanol and the filtrates are combined and concentrated in vacuo to remove the solvent and excess ammonia. The resultant viscous oil is diluted with ethanol and acetic acid, treated with 2-ethacrolein (19.5 g, 0.232 mol), heated at 70° C. for 6 hours and vacuum distilled at 60° C. to remove solvent. The resultant pot liquor is taken up in toluene, washed with water and concentrated in vacuo to afford a crude oil residue. Vacuum distillation of the oil residue affords the title product as a tan oil, bp 151°–152° C. at 2mm Hg.

EXAMPLE 3

Preparation of dialkyl substituted-2,3-pyridinedicarboxylate from dialkyl dichlorosuccinate Using essentially the same procedure as that described in Example 2 and substituting the appropriate dialkyl dichlorosuccinate and suitable α,β-unsaturated aldehyde, affords the following pyridinedicarboxylates of formula I.

| X | Y | Z | R |
|---|---|---|---|
| H | CH₃ | H | C₂H₅ |
| H | CH₂OCH₃ | H | CH₃ |
| H | CH₂Cl | H | C₂H₅ |
| H | H | H | C₂H₅ |

(Structure I: pyridine ring with Y at 5-position, X at 4-position, COOR at 3-position, COOR at 2-position, Z at 6-position)

The above compounds are identified by $^1$HNMR and IR spectographic analysis.

What is claimed is:

1. A process for the preparation of a compound of formula I

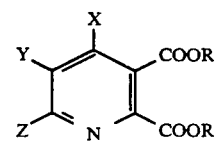

wherein R is C₁–C₆ alkyl; X is hydrogen, halogen, C₁–C₄ alkyl, C₁–C₄ alkoxy or C₂–C₅ alkenyl; Z is hydrogen, C₁–C₄ alkyl or C₂–C₅ alkenyl and Y is hydrogen, halogen, C₁–C₆ alkyl optionally substituted with one to three halogens, hydroxy groups, $C_1$-$C_4$ alkoxy groups or $C_1$-$C_4$ alkylthio groups, $C_1$-$C_4$ alkoxycarbonyl, aminocarbonyl, phenylthio, phenoxy, or phenyl which comprises reacting a dialkyl dichlorosuccinate of formula II

wherein R is $C_1$-$C_6$ alkyl with a dehydrohalogenating agent in the presence of a solvent to form a first intermediate, reacting said first intermediate with an ammonia source to form a second intermediate, reacting said second intermediate with an $\alpha,\beta$-unsaturated aldehyde or ketone of formula III

wherein X, Y and Z are as described above and an acid in the presence of the solvent, to form the formula I pyridinedicarboxylate compound.

2. The process according to claim 1 for the preparation of a formula I pyridinedicarboxylate compound wherein X and Z are hydrogen and Y is hydrogen, halogen or $C_1$-$C_4$ alkyl optionally substituted with one to three halogens, $C_1$-$C_4$ alkoxy groups or $C_1$-$C_4$ alkylthio groups.

3. The process according to claim 1 wherein the dehydrohalogenating agent is an ammonium salt, the solvent is a polar solvent and the acid is acetic acid.

4. The process according to claim 1 wherein the second intermediate is formed at a temperature of about 45° C. or greater.

5. The process according to claim 1 wherein the formula I pyridinedicarboxylate compound is formed at a temperature of about 45°0 C. or greater.

6. The process according to claim 1 wherein the $\alpha,\beta$-unsaturated aldehyde or ketone of formula III is present in the amount of at least one molar equivalent.

7. The process according to claim 2 wherein the formula I compound prepared is dialkyl pyridine-2,3-dicarboxylate.

8. The process according to claim 2 wherein the formula I compound prepared is dialkyl 5-methyl-2,3-pyridinedicarboxylate.

9. The process according to claim 2 wherein the formula I compound prepared is dialkyl 5-ethyl-2,3-pyridinedicarboxylate.

10. The process according to claim 2 wherein the formula I compound prepared is dialkyl 5-(methoxymethyl)-2,3-pyridinedicarboxylate.

11. The process according to claim 2 wherein the formula I compound prepared is dialkyl 5-(chloromethyl)-2,3-pyridinedicarboxylate.

12. The process according to claim 7 wherein the formula I compound prepared is diethyl pyridine-2,3-dicarboxylate.

13. The process according to claim 8 wherein the formula I compound prepared is diethyl 5-methyl-2,3-pyridinedicarboxylate.

14. The process according to claim 9 wherein the formula I compound prepared is diethyl 5-ethyl-2,3-pyridinedicarboxylate.

15. The process according to claim 10 wherein the formula I compound prepared is diethyl 5-(methoxymethyl)-2,3-pyridinedicarboxylate.

16. The process according to claim 11 wherein the formula I compound prepared is diethyl 5-(chloromethyl)-2,3-pyridinedicarboxylate.

* * * * *